United States Patent [19]

Peeler

[11] 4,139,000
[45] Feb. 13, 1979

[54] BLEEDABLE PRESSURE SYSTEM FOR MEASURING OR TESTING

[75] Inventor: Donald H. Peeler, Hendersonville, N.C.

[73] Assignee: Sybron Corporation, Rochester, N.Y.

[21] Appl. No.: 764,340

[22] Filed: Jan. 31, 1977

[51] Int. Cl.² ............................................. A61B 5/02
[52] U.S. Cl. .............................. 128/2.05 G; 73/748; 417/478
[58] Field of Search ............... 128/2.05 G, 2.05 A, 128/2.05 C, 2.05 M; 417/478; 73/402, 748

[56] References Cited

U.S. PATENT DOCUMENTS

| | | | |
|---|---|---|---|
| 3,633,567 | 1/1972 | Sarnoff | 128/2.05 C |
| 3,875,961 | 4/1975 | Gibbens | 128/2.05 G X |
| 3,906,939 | 9/1975 | Aronson | 128/2.05 G |

Primary Examiner—Lee S. Cohen
Attorney, Agent, or Firm—Theodore B. Roessel; Joseph C. MacKenzie

[57] ABSTRACT

A sphygmomanometric system having a pump for pumping air into a sphygmomanometer cuff connected to the cuff via a regulator valve for bleeding the cuff pressure at a constant rate. The pump has a leak to atmosphere so that the regulator valve can bleed the cuff through the pump. An exhaust valve is also provided for dumping the cuff pressure to atmosphere and/or bleeding the cuff, independently of the regulator valve.

16 Claims, 11 Drawing Figures

BLEEDABLE PRESSURE SYSTEM FOR MEASURING OR TESTING

Related Application

My copending application for U.S. Letters Patent, Ser. No. 764,341, assigned to the Sybron Corporation, filed the same day as the present application, and entitled "Fluid Pressure Measuring Or Testing System And Bleed Regulator Valve Therefor".

The detailed description of the present application is to be considered to contain the detailed description of its companion, above-identified.

Field of the Invention

My invention relates to measuring and testing by applying fluid pressure in a plenum physically related to the test subject or object and allowing the plenum pressure to bleed down at a predetermined rate. In particular, my invention relates to sphygmomanometry wherein the plenum is a cuff arranged on a living being for occluding an artery of such being. A pump is provided to pump the cuff up after which the air is released while Korotkow sounds, cuff pressures, and/or the like, are monitored.

Description of the Prior Art

My copending application describes and claims a sphygmomanometric system and regulator valve wherein the bleeding is regulated by the regulator valve. However, no particular means are provided for releasing the pressure in the cuff, save through the regulator valve, which creates inconveniences which the present invention is designed to remedy.

SUMMARY OF THE INVENTION

In the present invention, I provide the pump with a leak of sufficient magnitude such that if the pump is not being operated, the regulator valve, by virtue of the leak, operates with respect to about atmosphere pressure. Conversely, the leak is not so great that the pump can force appreciable air out the leak when being operated to pump up the cuff. In addition, I provide manually-operated exhaust valving to allow both bleeding off the cuff pressure, at a rate other than normally set by the regulator, and dumping the cuff pressure.

DESCRIPTION OF THE PREFERRED EMBODIMENT

Figure 1:
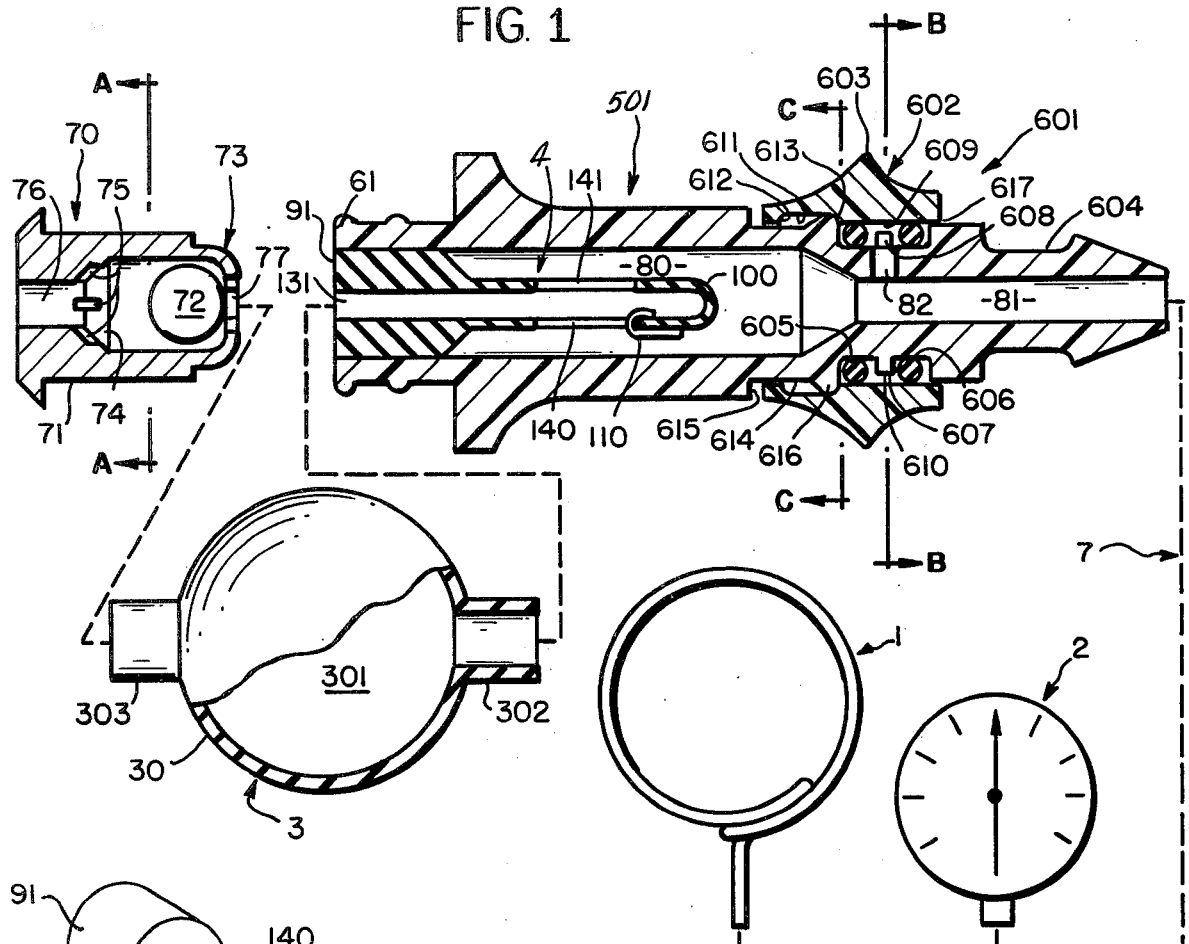
FIG. 1 is a partly schematic diagram of a bleedable pressure system according to my invention.
Figure 2:
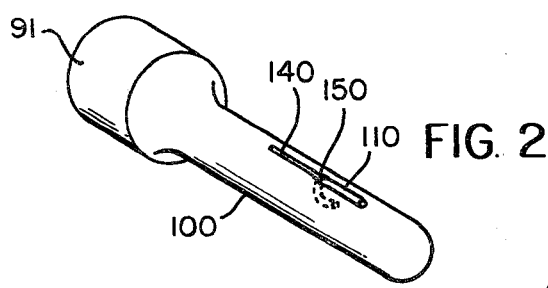
FIGS. 2 through 5 are detail views, of parts of FIG. 1, mostly sectional.
Figure 3:
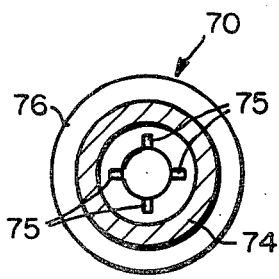
Figure 4:
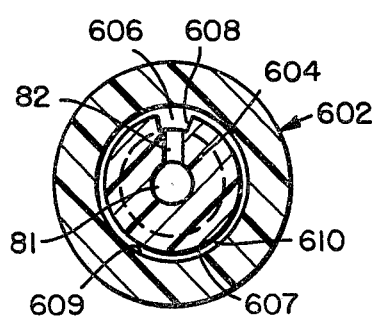
Figure 5:
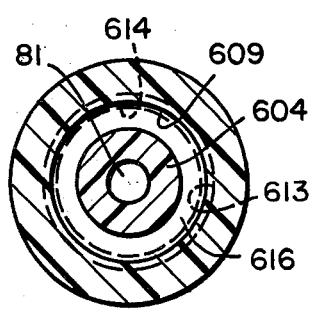

FIG. 1 shows my invention using, in the main, the elements of my sphygmomanometer system and regulator valve as described in my above-identified copending application, and comprising cuff 1, pressure gauge 2, pump 3, and regulator valve 4. Like in FIG. 4 of said application, the valve 4 has a nipple 100, slits 140 and 141, and variable opening 150 (see FIG. 2 hereof) created by "d"-shaped member 110 passing through one end of slit 140, and nipple 100 terminates in an integral annular base 91 which corresponds to fitting 90 of my other application. However, in this case, regulator valve 4 has housing 501 which unlike its counterpart 50 of my other application, instead of a simple end fitting 60 connecting to tubing 7, has a fitting 601, which includes exhaust valve structure described infra.

Like in my other application, pump 3 has a rubber or other elastomer bulb 30 hermetically fitted by an integral collar 302 over fitting 61 of regulator valve 4. Another integral collar 303 provides for receiving a check valve 70. Check valve 70 has the usual function of allowing air to be drawn into the interior volume 301 of bulb 30, when the bulb, after having been squeezed, is released and, to a degree, also has the usual function of preventing the air in interior volume 301 from being expelled to the atmosphere surrounding bulb 30, when the bulb is squeezed. However, the check valve, which has the general form of the usual fitting 71 having ball 72, cage 73, and conical seat 74, also has grooves 75 in the seat 74, so that when the ball is in the seat, grooves 75 prevent it from sealing off volume 301 from the external atmosphere. The atmosphere otherwise has access to volume 301 through fitting 70, via bore 76 into cage 73, around ball 72 which fits cage 73 sufficiently loosely as not impede air flow between it and the cage structure, which has opening 77 the form of which keeps the ball from sealingly seating therein at any time, but instead always will allow free flow of air therethrough, whether it be to or from interior volume 301.

It will be recalled from my above-identified other application that air can be forced, from inside nipple 100, out through slits 140 and 141, relatively freely, whereas air can be forced into the nipple 100 via opening 150, only restrictedly, because positive pressure, acting on the outside of the nipple, tries to hold the slits closed.

In other words, when the plenum formed by cuff 4, gauge 2, tubing 7, and chamber 80 contains a gas under pressure higher than that of the atmosphere surrounding such plenum, the gas will leak out of the plenum through regulator valve 4, provided pump 3 allows it, which in fact is the reason for providing a leaky check valve 70. More particularly, the flow resistance of the check valve, from volume 301 to atmosphere, with ball 72 seated and thereby allowing air flow solely through grooves 75, is chose to be less than would allow the pressure in volume 301 to build up enough above atmospheric pressure such as would prevent regulator 4 from regulating flow into chamber 80, from cuff 1, such that the pressure in cuff 1 bleeds down at a constant rate to the minimum useful or desired cuff pressure, for example, a value below the minimum expected diastolic pressure value, e.g., less than 40 mm. Hg gauge, say about 25 mm. Hg gauge.

Conversely, one expects to inflate the plenum to some super-atmospheric pressure, as in the case of cuff 1, where one would like to get the pressure to 300 mm. Hg gauge, before bleeding down. Accordingly, when one squeezes the bulb, the grooves 75 have to restrict flow to atmosphere enough to allow the pressure in volume 301 to get up to 300 mm Hg (the nipple 100 will be flexible enough that there is substantially nil resistance to air flow from inside the nipple out through the slits 140 and 141), so that the cuff can be pumped up to substantially the highest pressure that can be generated by compressing the bulb 30 in the presence of leakage through the check valve 70.

The foregoing is an important feature of my invention, as in sphygmomanometry it totally frees the user from the distracting activity of controlling the cuff bleed manually. Thus, at most, only the user's attention to sounds and gauge readings is engaged, uncomplicated by having to be concerned at how fast the cuff pressure is bleeding down.

However, it is also desirable to dump the cuff pressure. In sphygmomanometry, one sometimes encounters a subject whose medical condition is such that use of the cuff thereon is potentially dangerous to the subject's health, so one wants to be able to dump the cuff pressure, i.e., open it to atmosphere in some way which will allow the cuff pressure to drop to atmospheric pressure as quickly as possible, so as to release the stress it may be exerting on the subject. Also, once all the monitoring is done, with respect to any subject or object, one would prefer not to have to wait till the plenum bleeds down all the way to atmosphere. Thus, in sphygmomanometry, once diastole pressure has been determined, one would like to release the cuff, but it still may have air at a pressure of about 50 mm. Hg gauge in it.

For this reason, I provide the fitting 601 in the form of an exhaust valve, as well as in the form of a connector having passage 81 through which chamber 80 connects to tubing 7. The characteristic elements here are the air-impervious plastic sleeve 602 having an external flange-like bead 603 to provide a finger grip, and the side bore 82 through the wall of the main portion 604, of fitting 601, which can interconnect bore 81 with the atmosphere surrounding the main portion 604. O-rings 605 and 606, separated by flange 607 integral with main portion 604, flank a notch 608 in said disk, (through which notch the opening 81 has access to the space between the O-rings), and make a seal between the inner wall 609 of sleeve 602 and the external surface of main portion 604, so the air in the cuff cannot escape from bore 81, despite the fact that there is a substantial annular gap 610 between the peripheral surface of flange 607 and the inner surface 609 of sleeve 602.

An internal annular groove 611 in sleeve 602 provides the sleeve with internally projecting flange 612 and internal shoulder 613 flanking the groove 611. At the same time an external annular groove 614 on casing 501 provide the casing with an external shoulder 615 and an externally projecting flange 616 flanking flange 612 which projects into groove 614. Flange 616 is at the transition between body 501 and fitting 601 (which has a sort of external intermediate flange 617), and the two flanges flank the O-rings 605 and 606 and flange 607, thereby providing a sort of external groove about as wide as the internal surface 609 of sleeve 602 from shoulder 613 to the left side of flange 617, as portrayed in FIG. 1.

Except for O-rings 605 and 606 the internal surface 609 of sleeve 602 has enough clearance from casing 501 and main portion 604 as to slide smoothly thereon, left or right as far as groove 614 will permit (flange 612 projects into the groove 614). The aforesaid clearance is chosen to be enough so that if the sleeve 602 is moved far enough to the right (from the position shown in FIG. 1) so that the shoulder 613 is somewhere between O-rings 605 and 606, i.e., the surface 609 is clear of O-ring 606, then there will be substantially nil resistance to air flow out of cuff 1, etc., through such clearance, as at 617, for example. The bore 82 will be of such cross-sectional area as to offer minimum resistance to air flow therethrough.

The use and function of the exhaust valve structure of fitting 601 will be clear from the foregoing, so no further explanation or description of this feature of my invention is necessary.

Figure 6:
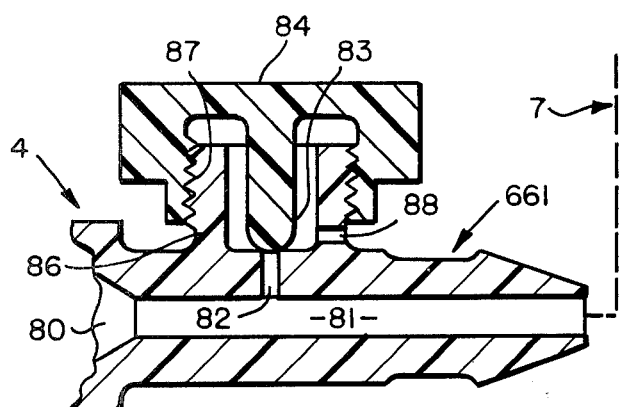
FIGS. 6, 7 and 8 are mostly sectional detailed views of exhaust valve structure useful in the system of FIG. 1, and FIGS. 9, 10 and 11 show details of one or another of FIGS. 7 and 8.

As thus far described, my invention aims at easing the demands sphygmomanometry makes on the user. However, some classes of skilled users are accustomed to total control of the rate at which air is released from the cuff. As shown in FIG. 6, such arrangement may be provided for by providing, instead of fitting 601, with its exhaust valve structure which provides for two rates of cuff pressure change therethrough (that is to say, nil and dump), I provide the fitting 661 in which the outer end of bore 82 can be sealed by a valve plug 83 carried internally by thumb nut 84 on a threaded fitting 86 surrounding the outer end of bore 82. By reason of the threading (indicated by reference numeral 87) the plug 83 can be backed out of a sealed position, where no air can flow out of bores 81 and 82, to a completely open position where the plug 83 is so far from the bore 82 that the only resistance to flow out of the bore 82 is the bore 88 through the wall of fitting 86, bore 88 however, being sufficiently large enough in cross-section as to offer substantially no resistance to flow therethrough.

Since the aforesaid completely open position is reached by turning thumb nut 84, it is evident that rates of bleed from cuff 1, which are intermediate the nil and dump rates, and also greater or lesser, as desired, than the rate at which bleed is permitted through regulator valve 4 (only very fragmentarily shown in FIG. 6). Thus, the skilled user, having pumped the cuff to 300 mm Hg gauge, while plug 83 is sealing the bore 82 and allowing no flow out of the bore 81, could then unscrew thumb nut 84 enough to allow air pressure to bleed through bores 82 and 88 at something less than the dump rate, but, when taken in conjunction with the rate at which the regulator valve is permitting bleed via pump 3, at a higher rate than would be desirable in the neighborhood of the systolic value. Before a likely value for systolic is reached the user might screw the plug back to where it again seals bore 82, and allow the regulator value to control the bleed rate until systole is detected. After systole is detected, the bore 82 may again be opened, in order to speed arrival in the vicinity of diastole, in which vicinity it will be again sealed until diastole is detected, upon which detection the bore 82 may then be opened completely to dump the remaining cuff pressure as fast as possible.

It may be noted, incidentally, that the above-described thumb nut exhaust valve structure and manual use thereof is in itself old in the art.

Figure 7:
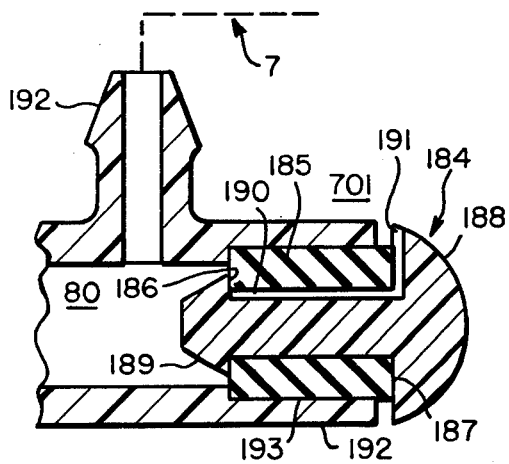
Figure 10:
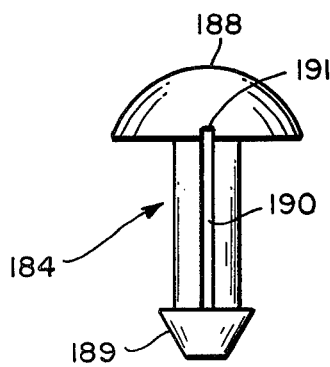
Figure 11:
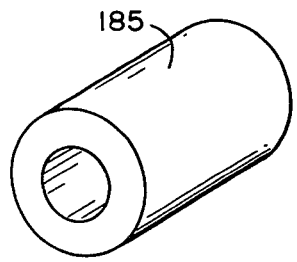

In FIG. 7, fitting 661 is replaced, in effect, with the fitting 701 having an exhaust value comprising a sort of bolt 184 (FIG. 10) on the shank of which is mounted cylindrical annulus 185 (FIG. 11) made of rubber or other elastomer. The distance between opposing faces of the bolt head 188 and the flange like element 189, integral with the rest of the bolt, is less than the length of the annulus 185, which, its ends being flat and the opposing surfaces of flange 189 and head 188 also being flat, come together to seal at interfaces 186 and 187, except for the longitudinal groove 190, running the entire length of the shank of the bolt and joining a groove 191 in the inside face of the head 188. Also, the inside face of flange 189 is substantially wider than the shank of the bolt 184, and interface 186 seals the adjacent end of the groove 190. However, the groove 191 opens beyond the interface 187 so is never sealed.

To operate the exhaust valve of FIGS. 7, it is necessary to force the bolt 184 to the left as by pushing on the head 188. As the annulus is sealingly mounted in a countersunk portion 192 of the fitting 701, so as to rest against an annular ledge 193 thereof 193, defined by the countersink, the interface 186 becomes a gap since the flange 186 moves to the left, whereas annulus 185, by reason of ledge 193, pretty much stays put. This means that air can flow out of the fitting 701, via the former interface 186, groove 190 and groove 191, because the surfaces forming the interface separate. This results in a bleed rate depending on how much interface 186 opens up, which in turn depends on the amount of force applied to head 188. If such force be released, the seal at interface 186 becomes reestablished and cuts off air flow therethrough.

Figure 8:
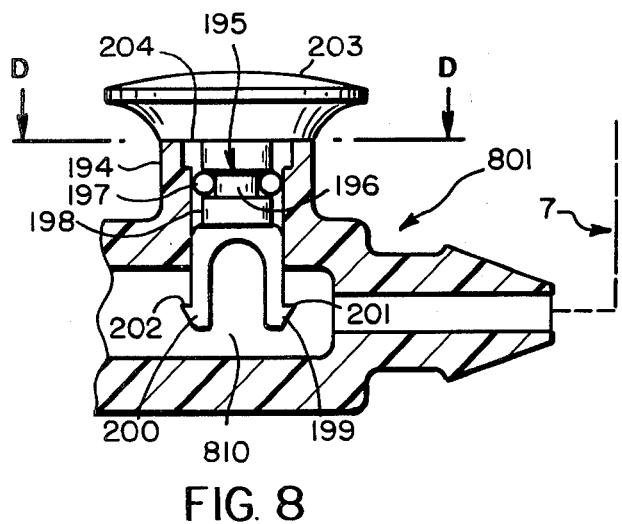
Figure 9:
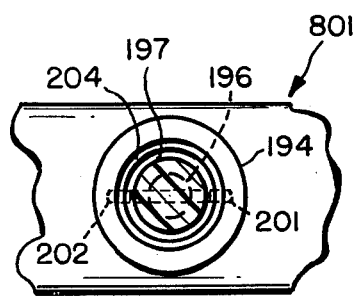

FIG. 8 is a reversion to FIG. 1, inasmuch as it shows a dump-only exhaust valve. In this case a fitting 801 carries a fitting 194 in which is mounted a piston 195 having an annular groove 196 therearound in which is mounted a rubber or other elastomeric O-ring 197. The piston 196 is loosely received in the cylindrical bore 198 of fitting 194. However, the inner and outer diameters are respectively more and less than the diameters of bore 198 and the grooved part of piston 195. As a result, the O-ring 197 seals bore 810 of fitting 801 off from the external atmosphere.

Legs 199 and 200, secured to piston 195, extend into bore 810 and lugs 201 and 202, spaced from the upper wall of the bore 810, and projecting into the length of the bore 810 far enough in both directions along the horizontal, that if the piston be lifted, as by a knob 203, it will only come out until the lugs 201 and 202 catch on the upper wall of bore 810, at which point O-ring 197 will be well within annular countersink 204 in the upper end of bore 198. The diameter of countersink 204 is enough greater than the diameter of O-ring 197 that air can flow, substantially unresisted, between the O-ring and the fitting in the annular space defined by countersink 204. As piston 195 and legs 199 and 200 fit freely, and offer no resistance to air flow, the cuff air can dump to atmosphere just as it does by means of FIG. 4's exhaust valve structure in fitting 601.

In the foregoing, certain elements have been described as being made of rubber or other elastomer, these elements being such that various amounts of substantially elastic deformation are desired of them for various purposes. Other structure which is static or at least not intended to be deformed appreciably, such as the fittings, and indeed all of the exhaust valve structure as shown in FIG. 6, is preferably metal or at least sufficiently rigid as not to affect the purposes served by deformation of the other elements. Naturally, the materials involved are intended to be impervious to air in view of the essence of present subject matter, namely transfer of air under pressure between a plenum immersed in a gaseous atmosphere, and that atmosphere.

I claim:

1. A bleedable pressure system having a plenum and also comprising a pump having a chamber the interior of which is variable in volume, said pump also having an inlet, and an outlet, said outlet being connected to said chamber and connecting the interior thereof to the interior of said plenum, and said inlet being connected to said chamber for connecting the interior thereof to an atmosphere surrounding said system;
said inlet incorporating therein a check valve means, said check valve means being responsive to decrease in interior volume of said chamber to substantially prevent communication between the interior of said chamber and said atmosphere;
said outlet incorporating therein a regulator valve means, said regulator valve means being responsive to decrease in interior volume of said chamber to open a substantial amount for admitting gas from the interior of said chamber to said plenum;
said check valve means being leaky, and said regulator valve means being responsive to regulated gas flow through said outlet from the interior of said plenum when the gas pressure in said plenum is greater than the gas pressure in the interior volume of said chamber, such as to cause gas pressure in said plenum to decrease at a predetermined substantially constant rate, said gas flow being less than leakage of said check valve means.

2. The bleedable pressure system of claim 1, including an exhaust valve means interconnecting said plenum and said atmosphere;
said exhaust valve means being manually adjustable to release gas from said plenum at a predetermined rate, greater than the rate at which gas can leak to said atmosphere, through said check valve means.

3. The bleedable pressure system of claim 2, wherein said exhaust valve means is operable to dump the gas in said plenum to said atmosphere.

4. The bleedable pressure system of claim 3, in combination with the inflatable cuff of blood pressure measuring system, said cuff being connected to said outlet as said plenum.

5. The bleedable pressure system of claim 3, wherein said pump is a manually-operated flexible bulb, and wherein the interior of said bulb is said chamber.

6. The bleedable pressure system of claim 3, in combination with the inflatable cuff of a blood pressure measuring system, wherein said cuff is connected to said outlet as said plenum, said wherein said pump is a manually-operable flexible bulb for inflating said cuff, the interior of said bulb being said chamber.

7. The bleedable pressure system of claim 2, in combination with the inflatable cuff of a blood pressure measuring system, said cuff being connected to said outlet as said plenum.

8. The bleedable pressure system of claim 2, wherein said pump is a manually-operated flexible bulb, and wherein the interior of said bulb is said chamber.

9. The bleedable pressure system of claim 2, in combination with the inflatable cuff of a blood pressure measuring system, wherein said cuff is connected to said outlet as said plenum, and wherein said pump is manually-operable flexible bulb for inflating said cuff, the interior of said bulb being said chamber.

10. The bleedable pressure system of claim 1, including an exhaust valve means connected to said plenum and being adjustable to release gas from said plenum at a rate of pressure decrease the value of which can range from nil to intermediate to dump.

11. The bleedable pressure system of claim 10, in combination with the inflatable cuff of a blood pressure measuring system, said cuff being connected to said outlet as said plenum.

12. The bleedable pressure system of claim 10, wherein said pump is a manually-operated flexible bulb, and wherein the interior of said bulb is said chamber.

13. The bleedable pressure system of claim 10, in combination with the inflatable cuff of a blood pressure measuring system, wherein said cuff is connected to said outlet as said plenum, and wherein said pump is a manually-operable flexible bulb for inflating said cuff, the interior of said bulb being said chamber.

14. The bleedable pressure system of claim 1, in combination with the inflatable cuff of a blood pressure measuring system, said cuff being connected to said outlet as said plenum.

15. The bleedable pressure system of claim 1, wherein said pump is a manually-operated flexible bulb, and wherein the interior of said bulb is said chamber.

16. The bleedable pressure system of claim 1, in combination with the inflatable cuff of a blood pressure measuring system, wherein said cuff is connected to said outlet as said plenum, and wherein said pump is a manually-operable flexible bulb for inflating said cuff, the interior of said bulb being said chamber.

* * * * *